(12) United States Patent
Kim

(10) Patent No.: US 7,685,735 B2
(45) Date of Patent: Mar. 30, 2010

(54) ELECTRONIC CALIPERS WITH ADJUSTABLE DIGITAL DISPLAY

(75) Inventor: John Y. S. Kim, Chicago, IL (US)

(73) Assignee: Eidosmed LLC, Chicago, IL (US)

( * ) Notice: Subject to any disclaimer, the term of this patent is extended or adjusted under 35 U.S.C. 154(b) by 253 days.

(21) Appl. No.: 12/027,379

(22) Filed: Feb. 7, 2008

(65) Prior Publication Data

US 2008/0184582 A1 Aug. 7, 2008

Related U.S. Application Data

(60) Provisional application No. 60/900,036, filed on Feb. 7, 2007.

(51) Int. Cl.
*G01B 5/00* (2006.01)

(52) U.S. Cl. ....................................................... 33/784

(58) Field of Classification Search .................. 33/783, 33/784, 810, 811, 819; D10/73
See application file for complete search history.

(56) References Cited

U.S. PATENT DOCUMENTS

| | | | |
|---|---|---|---|
| 2,920,395 A | 1/1960 | Germann | |
| 4,718,850 A | 1/1988 | Knebelman | |
| 5,056,238 A | 10/1991 | Chi | |
| 5,490,335 A | 2/1996 | Chu | |
| 5,873,175 A | 2/1999 | Johnston | |
| 6,043,438 A * | 3/2000 | Helberg | 177/148 |
| 6,990,746 B2 | 1/2006 | Penna et al. | |
| 7,076,886 B2 | 7/2006 | John et al. | |
| 7,306,366 B1 * | 12/2007 | Camenzind et al. | 374/141 |
| 2003/0088991 A1 | 5/2003 | Fullerton | |

* cited by examiner

*Primary Examiner*—Randy W Gibson
(74) *Attorney, Agent, or Firm*—Drinker Biddle & Reath LLP

(57) ABSTRACT

An electronic calipers is provided with an adjustable digital display. In an embodiment the calipers includes an elongated body and a display member that pivots or rotates relative to the elongated body. The display member may include a base member, which is coupled with the elongated body for translational movement along at least a portion of a length of the elongated body, and a display coupled with the base member for pivotal movement between a first orientation and a second orientation. In other embodiments, the calipers includes a display portion that rotates on the body portion through an angle of about 360°. In some embodiments the display portion may be a generally annular-shaped member that rotates and/or translates on the elongated body.

20 Claims, 4 Drawing Sheets

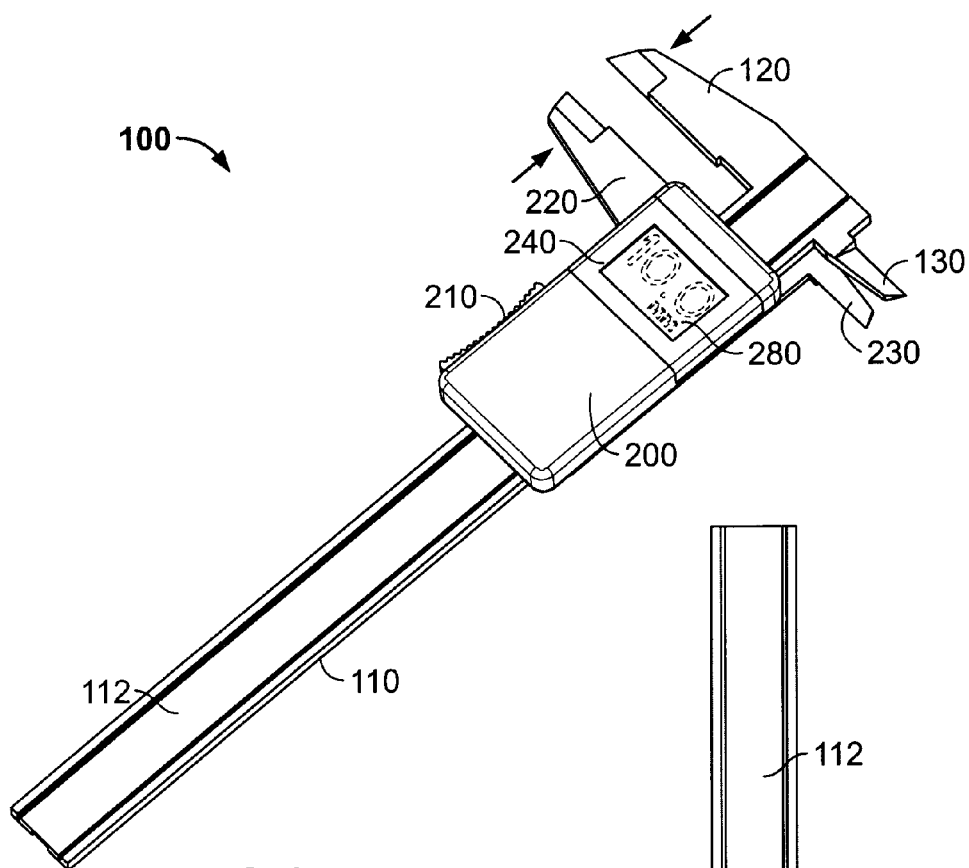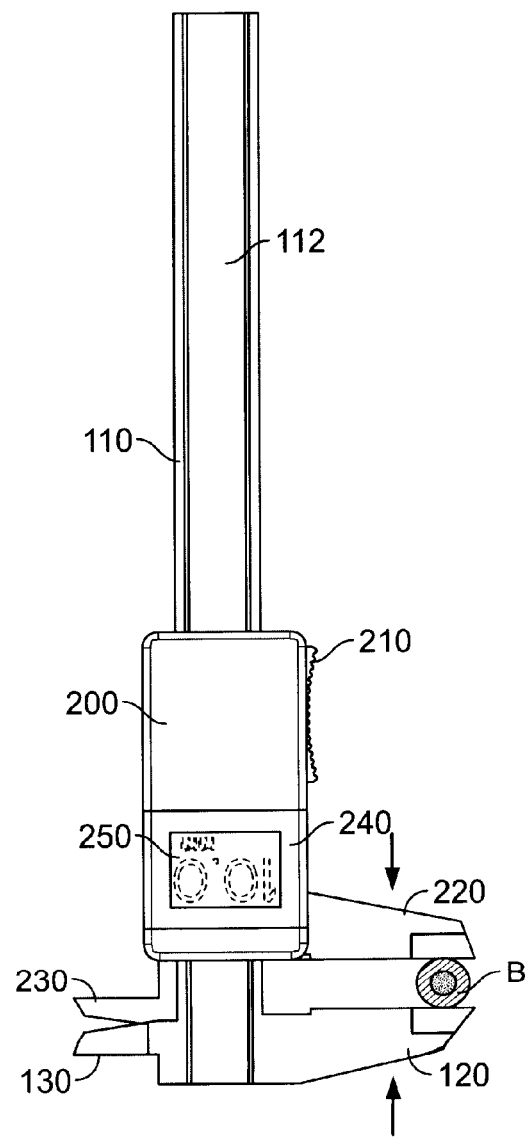
FIG. 1
FIG. 2

US 7,685,735 B2

ELECTRONIC CALIPERS WITH ADJUSTABLE DIGITAL DISPLAY

CROSS-REFERENCE TO RELATED PATENT APPLICATIONS

This patent application claims the benefit of U.S. Provisional Patent Application No. 60/900,036, filed Feb. 7, 2007.

FIELD OF THE INVENTION

This invention pertains generally to distance measuring devices. More particularly, the invention relates to electronic calipers.

BACKGROUND OF THE INVENTION

As is known, the digital display of conventional electronic calipers is configured on one side of a sliding member to which a movable jaw is coupled. Conventional electronic calipers (also known in the art as "digital" calipers) are typically used to measure an object which can be readily placed within its jaws. However, when dealing with an immovable object, which may be located in a restrictive environment (e.g., a bone in a surgical field), it may be difficult or impossible to see or read the display when the jaws of the calipers are clamped on the object. In one instance the object to be measured may be small and distal from the user. To measure the object, the movable jaw will be distal from the user, which makes the display difficult to see and read. In another instance the object to be measured may be accessible only from a certain direction (e.g., from above, below, etc.) due to a proximate object. Thus, when the caliper jaws are clamped on the object, the display may be upside-down, pointed away from the user or otherwise oriented so that it is difficult (or impossible) to see and/or read the display. For example, when a sternal bone is to be measured during a cardiothoracic surgical procedure, the bone (e.g., the sternum, clavicle, rib, etc.) may be accessible only from below and the jaws of the calipers are oriented upward so that the display is facing to the right. Now, to view the display the user must be able to position him or herself on the right side of the calipers, however this may not be convenient or may not even be possible. In view of the foregoing, electronic calipers with an adjustable digital display would be an important improvement in the art.

BRIEF SUMMARY OF THE INVENTION

An electronic calipers is provided with an adjustable digital display. In an embodiment the calipers includes a display portion that flips open from a body portion of the calipers and pivots through an angle of about 180°. In other embodiments, the calipers includes a display portion that rotates on the body portion through an angle of about 360°. In some embodiments, the display portion may rotate on the body portion and slide or translate along at least a portion of its length. In an embodiment the rotatable display portion may translate independently from a movable jaw to facilitate measurement of a small distal object.

BRIEF DESCRIPTION OF THE DRAWINGS

FIG. 1 shows a first embodiment of an electronic calipers with an adjustable digital display in a first orientation;

FIG. 2 shows the electronic calipers of FIG. 1 being used to measure an object;

DETAILED DESCRIPTION OF THE EMBODIMENTS

Referring now to the Figures, various embodiments of electronic calipers with an adjustable digital display are provided. Embodiments of the electronic calipers that are described and shown herein may be configured, assembled or otherwise constructed of suitable materials such as, for example, stainless steel or plastic, so that the calipers is sterilizable or disposable. Thus, embodiments of the calipers may be used advantageously in medical applications (e.g., orthopedic or cardiothoracic surgical procedures) to, for example, measure the dimension (e.g., length, thickness, outside diameter, etc.) of a bone so that an appropriately-sized drill bit, fastener, etc. may be selected. However, the calipers described and shown herein are not limited to such applications.

Figure 3:
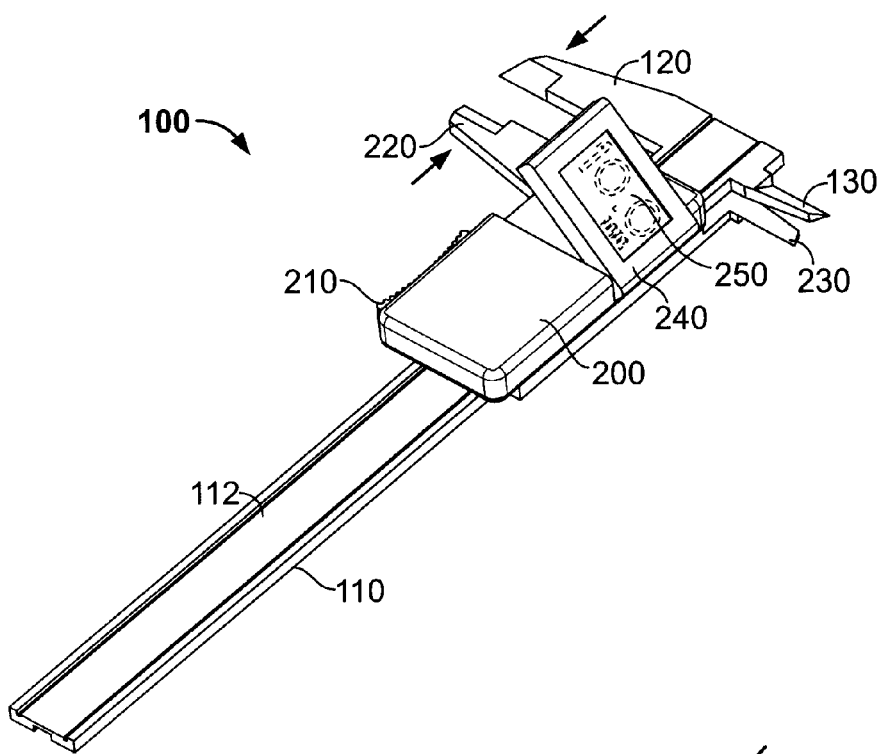
FIG. 3 shows the electronic calipers of FIG. 1 with the adjustable digital display being pivoted.
Figure 4:
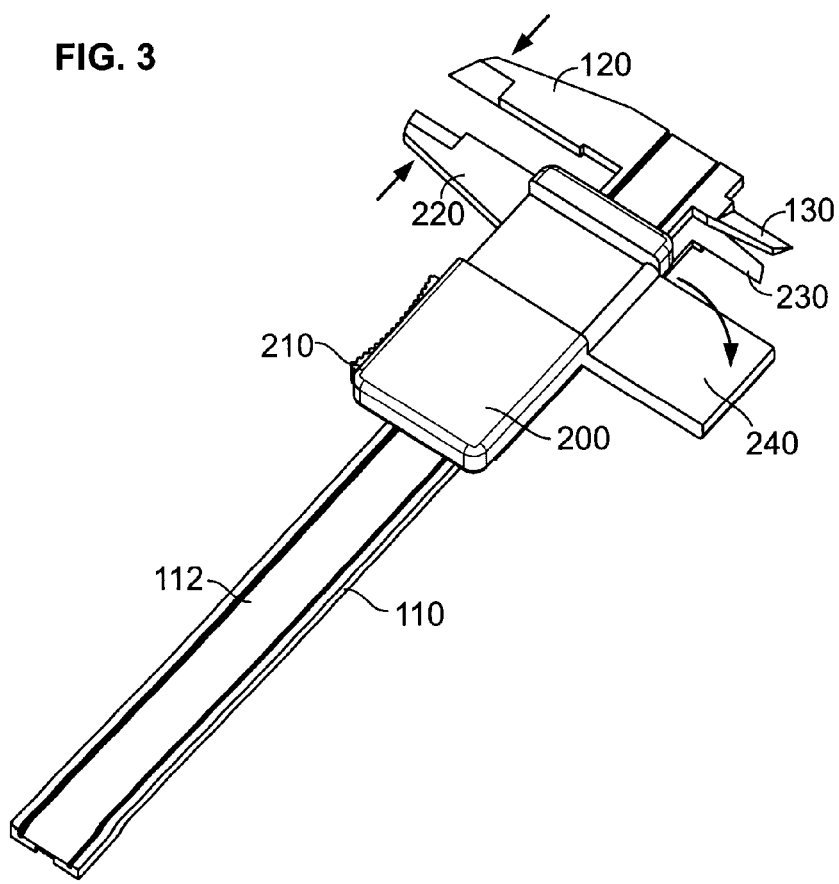
FIG. 4 shows the electronic calipers of FIG. 1 with the adjustable digital display in a second orientation.
Figure 5:
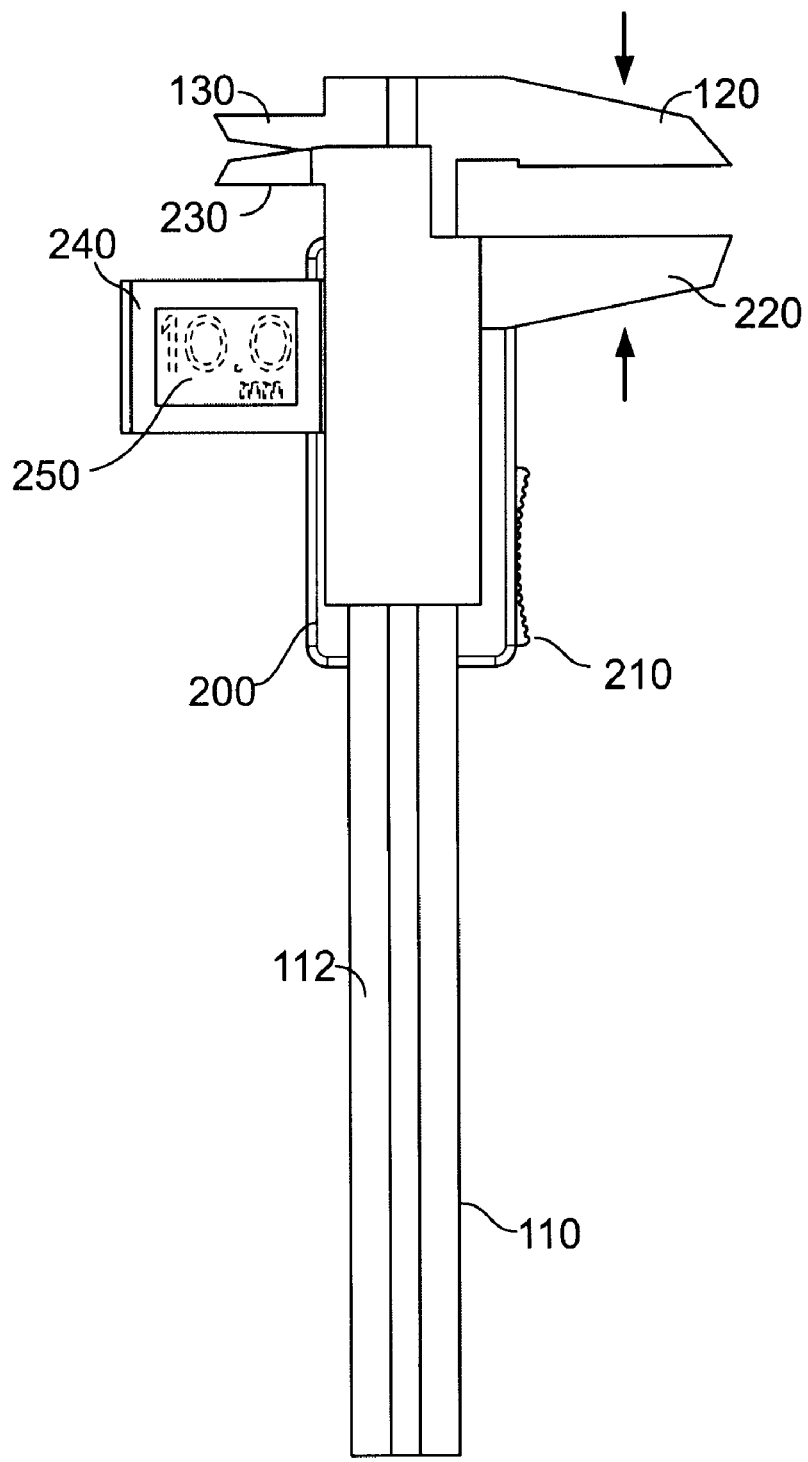
FIG. 5 shows an opposite side view of the electronic calipers of FIG. 4.
Figure 6:
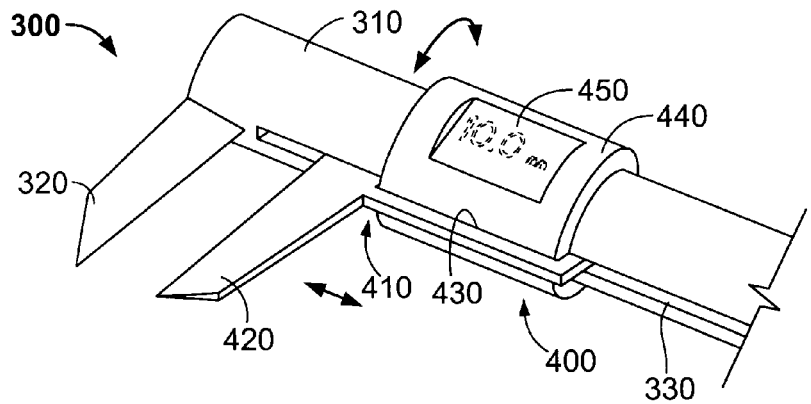
FIG. 6 shows a second embodiment of an electronic calipers with an adjustable digital display.
Figure 7:
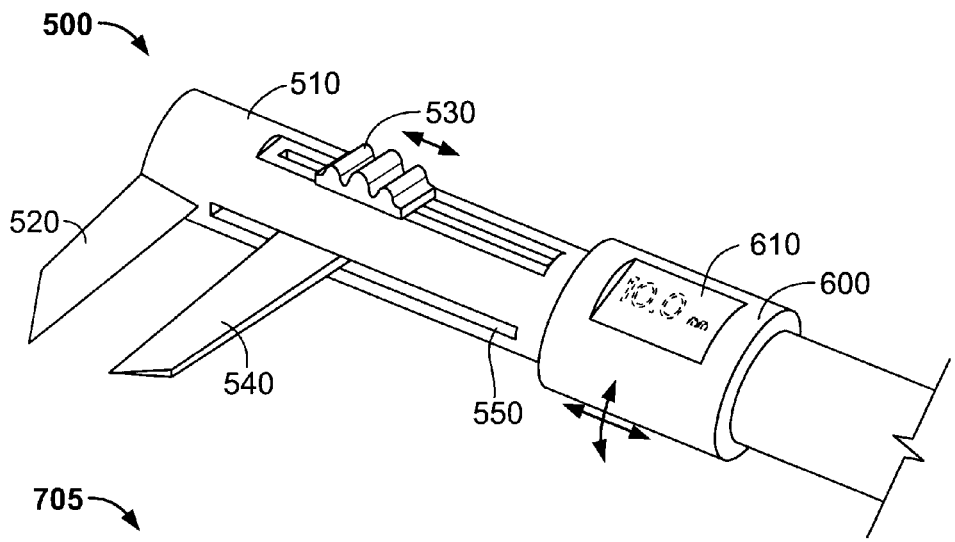
FIG. 7 shows a third embodiment of an electronic calipers with an adjustable digital display.
Figure 8:
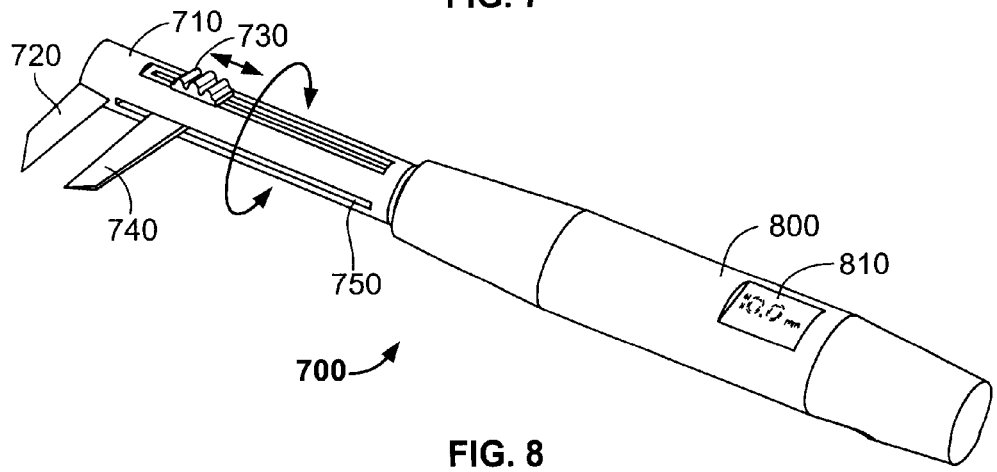
FIG. 8 shows a fourth embodiment of an electronic calipers with an adjustable digital display.

As shown in FIGS. 1-5, a first embodiment 100 of the electronic calipers includes a body portion 110 and a sliding member 200 that is coupled with the body portion 110 for sliding movement along substantially its entire length. The body portion 110 may be molded, formed, machined or otherwise configured of a stainless steel material so that the body portion 110 is sterilizable. Alternatively, the body portion 110 may be molded, formed, machined or otherwise configured of a plastic material so that the body portion 110 is considered as being disposable. In some embodiments, the sliding member 200 may be removable from the body portion 110 and have a sealed construction so that the sliding member 200 is separately sterilizable. As further shown, the body portion 110 is generally planar in shape and includes a first surface 112 and a second surface 114 (FIG. 5). As can be appreciated, the body portion may be configured otherwise (e.g., with a generally cylindrical shape as shown in FIGS. 6-8) as will be described hereinafter.

As shown, the body portion 110 includes at its distal end a first fixed jaw 120 and a second fixed jaw 130. The fixed jaws 120, 130 may be integral or unitary with the body portion 110. As further shown, the sliding member 200 is coupled with a first movable jaw 220 and a second movable jaw 230. In some embodiments the first and second movable jaws 220, 230 may be removably attached to the sliding member 200 so that the jaws 220, 230 may be disposed of or separately sterilized and reattached/reused. As should be appreciated, other features of the device might be separately disposable, such as the display or the jaws, while other features may be retained and be sterilized and reused with new disposable features. The first fixed jaw 120 and the first movable jaw 220 may be used to clamp on or otherwise contact an object for measuring an object's outer dimension (e.g., the outer diameter of a cylindrical pipe), whereas the second fixed jaw 130 and the second movable jaw 230 may be used for measuring a small or inside dimension (e.g., the inner diameter of a cylindrical pipe). Although the second fixed jaw 130 and the second movable jaw 230 are illustrated in FIGS. 1-5 and described herein, the calipers may not include the jaws 130 and 230 (see, for example, FIGS. 6-8). Furthermore, it should be appreciated that the terms distal (or distally) and proximal (or proximally) are simply used herein for sake of convenience and are not limiting on the described embodiments. To this end, although the distal jaw (first fixed jaw 120) is referred to as being fixed in this embodiment 100 of the calipers, in alternative embodiments the distal jaw may be movable while the proximal jaw is fixed. Indeed, in yet other embodiments, both of the distal and proximal jaws may be movable.

As known in the art, the calipers may employ any suitable sensing device for determining a distance that the sliding member 200 moves away from or toward the distal end. The sensing device may be for example a linear encoder, which may employ any one or more of acoustic, ultrasound, capacitive, electric field, inductive, electromagnetic (e.g., Hall effect-type) and optical components for determining relative or absolute distance measurements. Sensors and sensor assemblies that may be employed for the calipers are readily available commercially from manufacturers such as Sylvac and Mitutoyo. For example, capacitive and inductive readhead and write-head assemblies are used in digital calipers, such as that made by Mitutoyo America Corporation, 965 Corporate Blvd., Aurora, Ill., and by Guilin Measuring and Cutting Works, 106 Chongxin Road, Guangxi, Guilin 541002, Peoples Republic of China.

Although not illustrated, a first portion of the sensing device may be configured on the body portion 110 (e.g., one or both of the surfaces 112, 114). This first portion of the sensing device may be a passive element such as, for example an encoded strip, flexible circuit board with printed capacitive or inductive traces, etc. An active portion of the sensing device that reads or otherwise cooperates with the passive portion for determining a position of the sliding member 200 along the passive element may be configured in or on the sliding member 200. Thus, as the sliding member 200 moves along the length of the body portion 110, a distance between the facing surfaces of jaws 120 and 220 may be determined and displayed. As a reference for absolute measurements, when the facing surfaces of jaws 120 and 220 are abutting each other, a distance being measured by the calipers may be zero. However, a reset or zeroing actuator may be provided (e.g., on the sliding member 200) so that a user may "zero out" the measurement when the jaws 120, 220 are separated for measuring an incremental change in distance.

As further shown, the sliding member 200 includes a slide actuator 210 for moving the sliding member 200 along the length of the body portion 110, and an adjustable display portion 240 with a display 250. As shown, the slide actuator 210 includes a plurality of ridges for enhancing ergonomics and facilitating movement of the sliding member 200 by a user's thumb or finger. Although a plurality of ridges are shown, the slide actuator 210 may alternatively include a roughened surface, knurling, etc. that help a user grip and move the sliding member 200. The sliding member 200 may enclose various electronic and electrical components (not shown) of the calipers 100. Control and operational circuitry such as, for example a circuit board such as a PCB with a number of integrated circuit (IC) chips (e.g., a microprocessor, microcontroller, digital signal processor or the like) and other electronic and/or electrical components may be configured within the sliding member 200. Furthermore, a power source (not shown) such as rechargeable or disposable batteries may be configured in the sliding member 200 so that the calipers 100 may be used in an un-tethered/cordless manner. As can be appreciated, although not shown, the sliding member 200 may further include actuators (e.g., buttons, switches, etc.) that provide input signals to the internal circuitry of the calipers 100 to, for example, control operation of the display 250. Such actuators may be operated by the user for turning the calipers 100 on and off, resetting or zeroing a measurement, changing measurement units (e.g., inches, millimeters, etc.) and the like. The display 250 may be various display devices known in the art such as a liquid crystal display (LCD) panel, a thin film transistor (TFT), a light emitting diode (LED) array and the like. The display 250 may be configured to display a number of alphanumeric indicia for providing the user with a visual indication of a distance of an object (e.g., bone B shown in FIG. 2) that is being measured by the jaws 120, 220. As can be appreciated, in some embodiments the sliding member 200 may be environmentally sealed to prevent intrusion of contaminants such as, for example, fluids, fine particulate matter, etc. therein. Embodiments of the calipers that include an environmentally sealed sliding member 200 may advantageously be cleaned, washed, sterilized or the like and reused.

As is best illustrated in FIGS. 1 and 2, the adjustable display portion 240 of calipers embodiment 100 has a first orientation so that a user may view the display 250 from a vantage point looking toward the first surface 112. The display 250 may be disposed in a recess (as shown in FIGS. 3 and 4) defined in a surface of the display portion 240 when the display is positioned in the first orientation. Furthermore, as shown in FIGS. 3-5, it can be appreciated that the display portion 240 is movable from that first orientation to a second orientation. In particular, in the first embodiment 100 of the electronic calipers, the display portion 240 is coupled with the sliding member 200 for rotating or pivoting movement through a plurality of continuous or discrete orientations about an axis defined by an edge of the sliding member 200 (e.g., the edge opposite the sliding actuator 210) so that the display 250 pivotally moves about the axis. That is, similar to a display of electronic devices including camcorders and digital cameras, the display portion 240 flips up from the first orientation within the recess of the sliding member 200 and pivots to the second orientation. As shown, the display portion 240 may be adjusted through an angle of about one hundred eighty degrees (180°), however, the angle of adjustment may be greater. The display portion 240 may be movably connected or coupled with the sliding portion 200 by various hinges known in the art such as a leaf hinge, living hinge, butt hinge, butterfly hinge, continuous hinge, piano hinge, mortise hinge or the like. By pivoting the display portion 240 on the hinge, the display 250 may be viewed by the user from a vantage point looking toward the second surface 114 as shown in FIG. 5. In this way, the user need not remove the calipers 100 from the object being measured and reposition it upside-down (if it were even possible to do so due to adjacent obstructions) or reposition him or herself for conveniently viewing the display 250. As can be appreciated, a switch or sensor may be in communication with the hinge or the display so that the indicia being shown on the display 250 is adjusted (e.g., rotated) for convenient viewing and reading by the user.

Referring now to FIG. 6, in a second embodiment 300 of the electronic calipers, the calipers includes a body member 310 that is generally cylindrical in shape and a sliding member 400 that is coupled with the body member 310 for sliding movement along substantially its entire length. As shown, the body portion 310 includes at its distal end a fixed jaw 320. As further shown, the body portion 310 includes a slot 330 that extends proximally from (i.e., away from or toward the user) the fixed jaw 320. The sliding member 400 includes a member 410 that defines a movable jaw 420 and a proximally-extending portion which is configured in the slot 330 for translation along its length. The proximally-extending portion of member 410 includes an aperture 430 through which a generally annular display portion 440 extends. With the generally annular display portion 440 coupled with the member 410 as shown, the sliding member 400 is slidably movable proximally and distally on the body member 310 and the generally annular display portion 440 is substantially rotatable (e.g., 360°) about the body member 310 as is indicated by the double-headed arrows. In this way, the display 450 may be positioned for convenient viewing and reading by the user.

Referring now to FIG. 7, an embodiment of the calipers is provided in which the display may be adjusted with two degrees of freedom independently from the movable jaw. In a third embodiment 500 of the electronic calipers, the calipers includes a body member 510 that is generally cylindrical in shape, a fixed jaw 520 at a distal end of the body member 510, a slide actuator 530 and a movable jaw 540. The slide actuator 530 is coupled with the movable jaw 540 for slidably moving the movable jaw 540 along a substantially entire length of the slot 550. The slide actuator 530 may be disposed on the body of the device 500 at about the same position as the movable jaw 540, or, alternatively, the slide actuator 530 may be positioned with an internal linkage such that it is disposed further down the handle from the movable blade 540. Although the slot 550 is illustrated as extending along a small portion of body member 510, the slot 550 may be configured to extend a greater distance (e.g., substantially to the proximal end of the body member 510) so that the embodiment 500 of calipers may be used for measuring objects of various sizes and shapes. As further shown, the embodiment 500 includes a display portion 600 that has a generally annular shape. As indicated by the double-headed arrows, display portion 600 is coupled with the body member 510 for sliding movement thereon as well as substantial (e.g., 360°) rotational movement about a rotational axis defined by a central lengthwise axis through the body member 510. In this way, if the user is measuring a small distal object (e.g., a bone in a deep or obscured surgical field), the user may suitably orient the jaws 520, 540 (e.g., upward, downward, forward, etc.), move the slide actuator 530 to clamp the jaws 520, 540 on the object and move the display portion 600 rotationally and proximally (i.e., toward the user) for more convenient viewing and reading of the display 610.

Referring now to FIG. 8, another embodiment of the calipers is provided in which the display may be adjusted independently from the movable jaw. In a fourth embodiment 700 of the electronic calipers, the calipers includes a jaw portion 705 and a handle portion 800. The jaw portion 705 includes a body member 710 that is generally cylindrical in shape, a fixed jaw 720 at a distal end of the body member 710, a slide actuator 730 and a movable jaw 740. The slide actuator 730 is coupled with the movable jaw 740 for slidably moving the movable jaw 740 along a substantially entire length of the slot 750. As shown, the slot 750 extends along a substantial length of jaw portion 705 so that the embodiment 700 of calipers may be used for measuring objects of various sizes and shapes. As further shown, the embodiment 700 includes a handle portion 800 that is coupled with the jaw portion 705 at its proximal end. As indicated by the curved double-headed arrow, the jaw portion 705 and the handle portion 800 are coupled for substantial (e.g., 360°), relative rotational movement about a rotational axis defined by a central lengthwise axis through the handle and jaw portions 705, 800. In this way, the display portion 600 may be adjusted rotationally for more convenient viewing and reading of the display 610.

In the second, third and fourth embodiments 200, 500 and 700, the display portions may include a sensor that determines a direction that the display is facing so that the indicia being shown on the display is automatically adjusted (e.g., rotated, flipped, etc.) accordingly for convenient viewing and reading by the user. Alternatively or additionally, the display portions of embodiments 200, 500 and 700 may include an actuator (e.g., button, switch, etc.) that a user may operate for manually adjusting (e.g., rotating, flipping, etc.) the indicia being displayed as the user desires.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. An electronic calipers comprising:
    an elongated body including a first end, and a second end with a first jaw that extends generally perpendicularly from the second end;
    a second jaw coupled with the elongated body for movement along a length of the elongated body, the second jaw being parallel with the first jaw for clamping an object to be measured between the first and second jaws; and
    a digital display member coupled with the elongated body for pivotal movement relative to the first and second jaws.

2. The electronic calipers of claim 1 wherein:
    the elongated body is generally planar and includes a first side, and a second side generally parallel with the first side; and
    the digital display member includes a base member, and a display that indicates an indicia defining a measurement of the object between the first and second jaws, the display being coupled with the base member for movement between a first orientation wherein the display is viewable only from the first side, and a second orientation wherein the display is viewable only from the second side.

3. The electronic calipers of claim 2 wherein the digital display member further includes a hinge pivotally coupling the display and the base member.

4. The electronic calipers of claim 3 wherein the hinge is configured to pivot the display between the first and second orientations through an angle of about 180 degrees.

5. The electronic calipers of claim 2 wherein the base member further includes a recess into which the display is disposed when the display is in the first orientation.

6. The electronic calipers of claim 2 further comprising an orientation-determining member in communication with the display, the orientation-determining member discriminating between the first and second orientations for changing the indicia according to the first and second orientations.

7. The electronic calipers of claim 2 wherein the base member further comprises a slide actuator for moving the digital display member along a length of the elongated body.

8. The electronic calipers of claim 7 wherein the slide actuator includes an ergonomic treatment selected from the group consisting of ridges, knurling and surface-roughening.

9. The electronic calipers of claim 2 wherein the second jaw is integral with the digital display member.

10. The electronic calipers of claim 2 wherein the display is an LCD panel configured to display alphanumeric indicia.

11. The electronic calipers of claim 1 wherein:

the elongated body is generally cylindrical; and the digital display member includes a base member coaxially coupled with the elongated body for rotation relative to the first jaw, and a display on the base member that indicates an indicia defining a measurement of the object between the first and second jaws.

12. The electronic calipers of claim 11 wherein the digital display member extends from the first end the elongated body.

13. The electronic calipers of claim 11 wherein the digital display member is generally annular and coaxially configured on the elongated body, the display member being translatable along at least a portion of length of the elongated body.

14. An electronic calipers comprising:

an elongated generally planar body including a first end, and a second end with a first jaw that extends generally perpendicularly from the second end;

a sliding member coupled with the elongated body for movement along a length of the elongated generally planar body, the sliding member including a second jaw parallel with the first jaw, and a housing enclosing electronic components, the electronic components determining a distance between the first and second jaws; and a digital display member coupled with the elongated body for pivotal movement relative to the housing, the digital display member receiving signals from the electronic components for displaying an indicia relative to the distance between the first and second jaws.

15. The electronic calipers of claim 14 wherein the digital display pivots between a first orientation wherein the display is viewable only from a first side of the elongated body, and a second orientation wherein the display is viewable only from a second side of the elongated body.

16. The electronic calipers of claim 15 further comprising a hinge pivotally coupling an edge of the digital display member with an edge of the housing.

17. The electronic calipers of claim 16 wherein the hinge is configured to pivot the digital display member between the first and second orientations through an angle of about 180 degrees.

18. The electronic calipers of claim 14 wherein the housing further includes a recess into which the digital display member is disposed when the display is in the first orientation.

19. The electronic calipers of claim 15 further comprising an orientation-determining member in communication with the digital display member, the orientation-determining member discriminating between the first and second orientations for changing the indicia according to the first and second orientations.

20. The electronic calipers of claim 14 wherein the second jaw is integral with the housing.

* * * * *